(12) United States Patent
Revol-Cavalier et al.

(10) Patent No.: US 10,292,869 B2
(45) Date of Patent: May 21, 2019

(54) ARTICLE FOR ABSORBING A PHYSIOLOGICAL LIQUID, SUCH AS A DRESSING

(71) Applicants: COMMISSARIAT A L'ENERGIE ATOMIQUE ET AUX ENERGIES ALTERNATIVES, Paris (FR); URGO RECHERCHE INNOVATION ET DEVELOPPEMENT, Chenove (FR)

(72) Inventors: Frédéric Revol-Cavalier, Seyssins (FR); Michel Lamoise, Bessey les Citeaux (FR); Cyril Marsiquet, Roumazieres Laubert (FR); Jean-Marc Pernot, Dijon (FR); Julien Steinbrunn, Messigny et Vantoux (FR)

(73) Assignees: COMMISSARIAT A L'ENERGIE ATOMIQUE ET AUX ENERGIES ALTERNATIVES, Paris (FR); URGO RECHERCHE INNOVATION ET DEVELOPPEMENT, Chenove (FR)

( * ) Notice: Subject to any disclaimer, the term of this patent is extended or adjusted under 35 U.S.C. 154(b) by 330 days.

(21) Appl. No.: 15/105,380

(22) PCT Filed: Dec. 16, 2014

(86) PCT No.: PCT/IB2014/066949
§ 371 (c)(1),
(2) Date: Jun. 16, 2016

(87) PCT Pub. No.: WO2015/092670
PCT Pub. Date: Jun. 25, 2015

(65) Prior Publication Data
US 2016/0374860 A1 Dec. 29, 2016

(30) Foreign Application Priority Data
Dec. 19, 2013 (FR) ..................................... 13 63014

(51) Int. Cl.
*A61F 13/00* (2006.01)
*A61F 13/02* (2006.01)

(52) U.S. Cl.
CPC .. *A61F 13/00029* (2013.01); *A61F 13/00068* (2013.01); *A61F 13/022* (2013.01)

(58) Field of Classification Search
CPC .......... A61F 13/00029; A61F 13/00042; A61F 13/00068; A61F 13/0206; A61F 13/0209;
(Continued)

(56) References Cited

U.S. PATENT DOCUMENTS

2003/0088229 A1  5/2003  Baker et al.
2011/0077571 A1  3/2011  Andresen
(Continued)

FOREIGN PATENT DOCUMENTS

DE   202012101743 U1   8/2012
EP        541391 A1    5/1993
(Continued)

OTHER PUBLICATIONS

Mar. 19, 2015 International Search Report issued in International Patent Application No. PCT/IB2014/066949.

Primary Examiner — Catharine L Anderson
(74) Attorney, Agent, or Firm — Oliff PLC

(57) ABSTRACT

An article having properties allowing same to absorb a body fluid. The article includes at least three paths for the propagation of fluid from a fluid capture zone to at least one storage and/or evaporation area, each fluid propagation path being delimited by a fluid barrier preventing the passage of liquid from one path to another.

13 Claims, 2 Drawing Sheets

Figure 1:
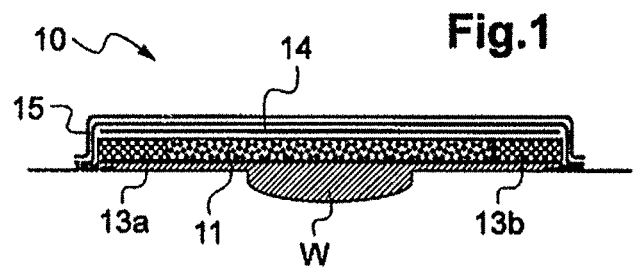

(58) Field of Classification Search
CPC .............. A61F 13/0213; A61F 13/0216; A61F 13/022; A61F 13/0223; A61F 13/533; A61F 13/536; A61F 2013/53782
See application file for complete search history.

(56) References Cited

U.S. PATENT DOCUMENTS

| | | |
|---|---|---|
| 2012/0136326 A1 | 5/2012 | Croizat et al. |
| 2014/0188090 A1 | 7/2014 | Riesinger |
| 2014/0276491 A1* | 9/2014 | Luckemeyer ..... A61F 13/00068 604/319 |

FOREIGN PATENT DOCUMENTS

| | | |
|---|---|---|
| WO | 00/42958 A1 | 7/2000 |
| WO | 2010/147533 A1 | 12/2010 |
| WO | 2012/140377 A1 | 10/2012 |
| WO | 2014/016759 A1 | 1/2014 |

* cited by examiner

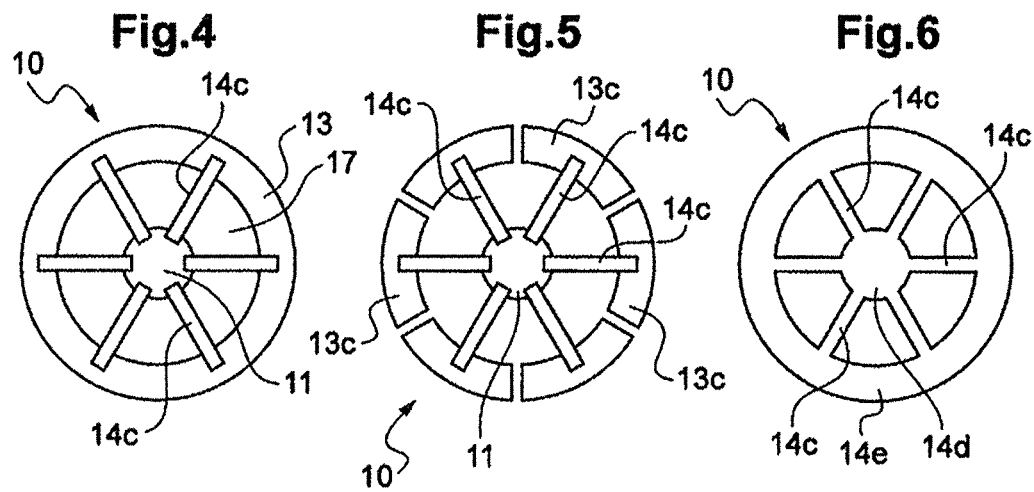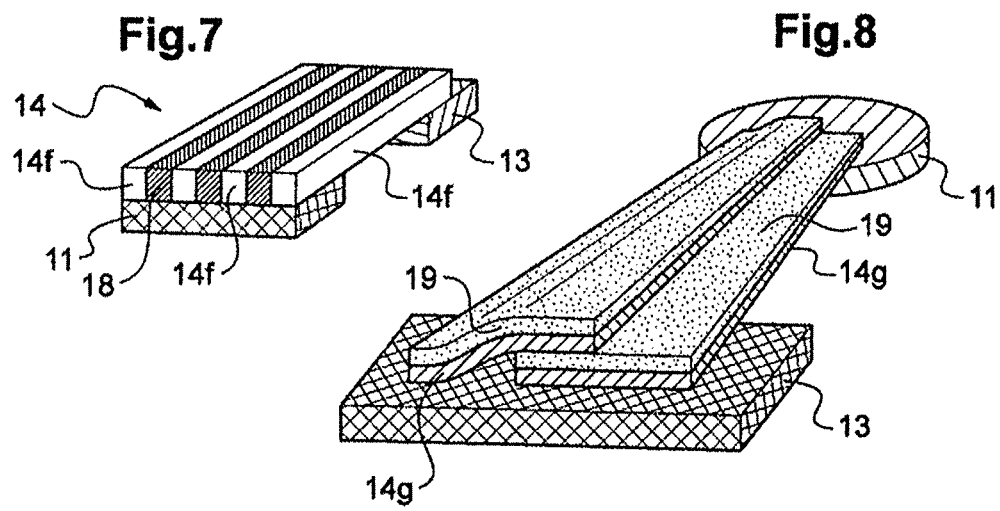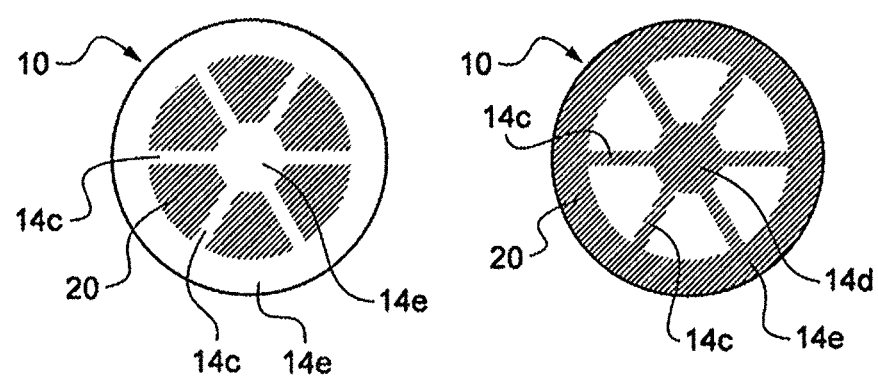

ARTICLE FOR ABSORBING A PHYSIOLOGICAL LIQUID, SUCH AS A DRESSING

The present invention relates to articles intended to come into contact with physiological liquids, particularly liquids secreted by the skin, a wound and/or the mucous membranes in order to manage the propagation, retention and/or evaporation of these liquids and, more particularly although not exclusively, to dressings to be applied to a wound.

The management of the propagation of liquids and retention thereof are complex problems to resolve for which the articles proposed in the field of hygiene products and dressings do not to date provide entirely satisfactory solutions.

These articles have indeed to meet a set of specifications which contains antagonistic requirements A first requirement is that the liquids be removed as quickly as possible to as far away as possible to prevent any maceration or irritation of the skin, of the wound or of the mucous membranes caused by the buildup of such liquids. Not only must the liquids not be allowed to accumulate, but it is also preferable to avoid their lateral migration from the site of secretion, so that they do not increase the extent of the moistened zone, this being for the purposes of guaranteeing better hygiene and contributing to the comfort of the user.

This is particularly important in the use of a dressing. In that case, it is of primordial importance to prevent the skin situated around the borders of the lesion, referred to as the perilesional skin, which is very fragile, from becoming moist, because that could damage it, for example encouraging infection and/or irritation.

Thus, it is desirable for the dressing to be effective at draining bodily liquids secreted by the wound away from the site at which they were secreted toward the periphery of this site. Such drainage ensures better hygiene and better conditions for healing.

A second requirement is for these liquids to be retained and prevented from returning to the skin, the wound or the mucous membranes. Significant retention makes it possible to increase the length of time for which the article is used. In the case of a dressing, this length of use is of particular importance because it makes it possible to reduce the risk of impairing the wound healing process by changing the dressing less frequently.

It is therefore desirable to have available articles that make it possible to manage the propagation and retention of liquids, particularly liquids secreted by a wound, the skin or the mucous membranes, by removing these liquids from their point of secretion in order to prevent them from accumulating and to increase the length of use of the article.

In order to remain over a wound for as long as possible, the dressing needs to allow significant drainage of liquids. This drainage is the sum of its absorption capacity and its capacity to eliminate the liquids retained in an absorbent layer in contact with the wound, by the evaporation of water vapor through a protective support of the dressing, which protects the wound and the absorbent layer from the external environment (bacteria, water, etc.).

EP 541391 proposes incorporating between the absorbent layer and the support a layer that encourages the spreading of the liquids in order to optimize the evaporation thereof. However, that solution is far from optimal because when the spreading layer is saturated with water, evaporation becomes less effective and, above all, the liquids have a tendency to drop back down into the parts of the absorbent layer that are not yet in contact with the liquids. This once again presents the risks associated with the accumulation of liquids at the wound and in the region of the perilesional skin, such as, for example, maceration and the possibilities of infection. It also reduces the absorption capacity of the absorbent layer, or even causes it to deform, following the creation of liquid content gradients within it.

In order to avoid these problems and increase drainage, it has therefore been proposed that the absorption capacity of the dressing be modified by superposing several absorbent layers. This solution offers the advantage, by manipulating the difference in absorption of two layers or the thickness of the first layer that comes into contact with the wound, of removing the liquids from the wound and preventing the maceration or infection problems associated with their presence at the wound and the perilesional skin.

In order to increase this liquid "pumping" effect, it has been proposed that a spreading layer be incorporated between the absorbent layer in contact with the wound and the absorbent layer superposed with it and which acts as a reservoir. Such a dressing was, for example, marketed by the company MOLNLYCKE Health Care at the beginning of the 2000s under the trade name Mepilex Border.

In order to optimize the drainage of this dressing, patent application WO 2010/147533 proposed the addition of a new liquid spreading layer between the reservoir layer and the support.

However, the solutions proposed are still far from being completely satisfactory. The increase in the number of superposed layers leads to thicker dressings in which the risks of leakage are increased. Now, it is desirable to have products that are as thin and flexible and compliant as possible so that they conform readily to the anatomy of the body region to which they are applied.

Optimizing the retention capacity also, because of the buildup of liquids, leads to heavier articles for which the risks of detachment because of the weight in the case of an adhesive dressing, for example because the dressing is positioned vertically on a leg ulcer or on a non-planar part of the body, are increased. In order to counter this deficiency, the adhesion of the adhesive would need to be increased. However, increasing the adhesion of a dressing is always a difficult matter because it is necessary to strike the right balance between high adhesion in order to guarantee that the dressing does not become detached and adhesion that is weak enough that the perilesional skin and the wound healing process are not damaged when the dressing is removed.

In addition, the presence of the reservoir layer decreases the overall permeability to water vapor of the dressing, even if a spreading layer is added between the support and the reservoir layer.

Finally, while such a structure of dressing does allow liquids to be removed from the wound, this increase in the liquid "pumping" capacity may, when the level of exudation of the wound decreases, or if the dressing is used on a wound that exudes less, cause the bed of the wound to dry out, something which is disadvantageous to the healing process.

Thus, even though the use of a spreading layer has been envisioned since the start of the 1990s in order to encourage the drainage of a dressing, a fully satisfactory product has yet to be developed.

Moreover, the presence of a spreading layer, made up of a draining strip, makes it possible to spread the liquid over the entire surface of this layer so that it may be rapidly transported from a collection zone to a retention zone. In principle, the surface of the spreading layer quickly becomes moistened, something which is advantageous if the liquid is to be spread or drained rapidly, although that may also become a disadvantage if this layer covers parts of the dressing that should not become moistened. Specifically, the spreading layer may redistribute the liquid that it carries over dry parts of the dressing before transferring them to the retention zone.

US 2011/0077571 A1 discloses a dressing comprising two draining strips made of an absorbent material which respectively lead from an absorbent layer positioned over the wound to two remotely-situated reservoirs. The two strips are superposed without the interposition of a moisture-proof barrier between them and this allows liquid to pass from one strip to the other when there is contact between them. This leads to a risk of liquid from one of the strips returning to a still-dry zone of the absorbent layer, via the other strip.

It is desirable to have available a dressing the structure of which makes it possible to prevent the accumulation of liquids at the wound and around the latter, while at the same time offering good permeability to water vapor and which is thin, compliant, and may be used whatever the level of exudation of the wound.

The invention seeks to create articles, particularly dressings, that meet the abovementioned objective. These dressings are preferably packaged in the sterile state.

The invention also seeks to improve hygiene articles other than dressings, such as disposable nappies or feminine sanitary products, by offering a high rate of absorption of bodily leakages, without detracting from user comfort.

One subject of the invention is an article having bodily-fluid absorption properties, comprising at least three fluidic-propagation paths leading from a zone in which said fluid is collected to at least one retention and/or evaporation zone, each fluidic-propagation path being delimited by a fluidic barrier opposing the passage of liquid from one path to another.

The article may be configured to absorb an exudate emitted by a wound, and to constitute a dressing.

The invention makes it possible to reduce the risk of liquid from the collection zone being propagated elsewhere than toward the retention and/or evaporation zone and the risk of moistening a dry part of the article in contact with the skin elsewhere than in the collection zone.

In the invention, the liquid which is disseminated for preference along a first fluidic-propagation path does not reach the adjacent fluidic-propagation path or paths or reaches same only to a very small extent. This then, when these paths have not yet been used and are dry, for example, avoids them absorbing a certain quantity of liquid to the detriment of the retention and/or evaporation zone to which the first fluidic-propagation path leads.

For that purpose, the fluidic barrier according to the invention may comprise an empty space and/or a hydrophobic material. The fluidic barrier may extend between two adjacent fluidic-propagation paths.

The invention may make it possible to reduce the extent of the surface of the article that is moistened by the liquid elsewhere than in the collection zone and the retention and/or evaporation zone. The comfort afforded by the article is improved and, in the case of a dressing, that may allow it to be left in place for longer.

The invention makes it possible to optimize the transfer of some of the fluid absorbed by the article to one or more absorbent parts defining the retention and/or evaporation zone also referred to as reservoir(s). This or these absorbent parts may be juxtaposed with the collection zone or alternatively situated remotely so as to make them easier to replace, as appropriate.

According to the invention, the transfer of the liquid takes place at a flow rate that is higher along a fluidic-propagation path than it is from one path to the other. This may be achieved by using, for the fluidic-propagation paths, disjointed elements of a transfer structure such that the liquid cannot, through lack of continuity of absorbent material between them, diffuse from one element to another.

Another way is to make the elements of the transfer structure from a material that has liquid drainage properties that differ according to the position of the material. For example, the material is hydrophilic along the fluidic-propagation paths and hydrophobic between the said paths, so that passage of liquid from one part to another is impeded. The paths may be formed by locally treating a hydrophilic porous material in such a way as to define hydrophobic zones extending between the hydrophilic zones, the latter defining the fluidic-propagation paths. As an alternative, the paths are formed by locally treating a hydrophobic porous material in such a way as to define hydrophilic zones constituting the fluidic-propagation paths.

The blocking of the diffusion of liquid from one path to the other may be total, notably in the case of disjointed elements, or just partial, for example in the case of locally different properties of the material defining propagation paths.

The liquid drained by the fluidic-propagation paths may be transferred to the retention and/or evaporation zone rather than being redistributed in part over the article while it is being transported, this constituting a first advantage of the invention, as indicated hereinabove.

Another advantage is that the transfer structure that defines these paths has the possibility of not completely covering the article, thereby improving its breathability, particularly when these paths are defined by disjointed elements. Disjointed elements means elements separated from one another by an empty space. The term empty denotes the absence of material. In particular, the empty space may be full of air.

The fluidic-propagation paths may be arranged substantially parallel to one another and/or with possible mutual imbrication of the paths. The paths may even be arranged with an angular offset about a center of the article, preferably then being evenly angularly distributed.

When the paths are arranged substantially parallel to one another they may define two sets of fluidic-propagation paths leading between a common fluid collection zone and two respective retention and/or evaporation zones, each retention and/or evaporation zone being specific to one of the two sets, the paths interpenetrating at the common collection zone.

When the paths are arranged with an angular offset, the fluidic-propagation paths may extend from a common fluid collection zone toward a common retention and/or evaporation zone so that the retention and/or evaporation zone completely surrounds the collection zone, the two zones being, for example, concentric. As an alternative, each path may drain the liquid toward a retention and/or evaporation zone specific to it.

The fluid collection zone is preferably tailored to the form of the source of the fluid. For example, in the case of a wound resulting from an incision or a cut, the collection zone may be of elongate shape. In the case of an article to be applied to a non-planar part of the body, the collection zone may conform to the relief of the relevant part of the body.

The number of fluidic-propagation paths is, for example, comprised between 3 and 10, to 50, or even 100. This number is notably dependent on the surface area of the collection zone.

The fluidic-propagation paths may be defined by elements that are at least partially superposed in order to optimize the surface area of the article. A material that is impermeable to water may then limit, or better still prevent, the transfer of liquid from one element to another element superposed with it.

In another alternative form, the fluidic-propagation paths are defined by elements each of the two ends of which opens onto an absorbent part forming a retention and/or evaporation zone. The fluid collection zone is then situated between the two absorbent parts forming retention and/or evaporation zones, in contact with part of the underside of the elements.

The collection zone of the article may be defined by a receiving absorbent part. The retention and/or evaporation zone of the article may be defined by at least one absorbent part forming a retention and/or evaporation zone.

Receiving Absorbent Part and Absorbent Part Forming a Retention and/or Evaporation Zone.

The receiving absorbent part is also termed an "absorbent layer" and the absorbent part forming a retention and/or evaporation zone is also termed a "reservoir-forming layer" or "reservoir". The term "layer" is to be understood as encompassing a monolayer arrangement or several assembled sublayers.

The receiving absorbent part and the absorbent part forming a retention and/or evaporation zone each preferably have a water absorption capacity greater than or equal to 500 $g/m^2$, better still greater than or equal to 800 $g/m^2$. They may contain or consist of any material capable of retaining liquids, such as for example the materials used in the field of hygiene and dressings.

The absorbent part forming a retention and/or evaporation zone may be defined by a material having a liquid absorption capacity greater than that of the transfer structure. The same is true of the receiving absorbent part. Thus, the water absorption capacity, in $g/m^2$, of the transfer structure is preferably less than that of the receiving absorbent part and than that of the absorbent part forming a retention and/or evaporation zone.

By way of example, mention may be made of absorbent foams and preferably hydrophilic polyurethane foams, all materials based on superabsorbent polymer (SAP), such as, for example, absorbent nonwovens incorporating particles of SAP, commonly used in the field of hygiene, absorbent textiles such as, for example, nonwovens based on viscose, rayon or cellulose, such as, for example, a wadding or hydrogels.

Within the context of the present invention it is preferable to use by way of receiving absorbent part a cellular material, for example a hydrophilic polyurethane foam, after the manner for example of the one marketed under the trade name MCF.03 by the company Advanced Medical Solution.

For the absorbent part forming a retention and/or evaporation zone it is preferable to use a material containing a superabsorbent polymer SAP.

The use of nonwovens obtained by the dry route method of manufacture known as the "airlaid" method, which contain particles of SAP and, in particular, between 20 and 60 wt % of SAP with respect to the total weight of the nonwoven is preferable. Such nonwovens are, for example, marketed by the company EAM Corporation under the reference Novathin®.

According to one preferred embodiment of the invention, use is made, for creating the absorbent part forming a retention and/or evaporation zone, of a nonwoven based on superabsorbent polymer particles and cellulose fibers without the incorporation of thermal binder or latex materials, and which is covered on each of its faces with a cellulose gauze.

According to an alternative form, a material consisting of two cellulose gauzes between which particles of superabsorbent polymers, alone or in combination with binders, are incorporated is used by way of SAP-based material.

According to another alternative form, a material based on SAP fibers alone or combination with non-absorbent fibers is used. For preference, this material takes the form of a nonwoven.

In order to conform as best as possible to conventional wounds, notably wounds resulting from cuts or incisions, the receiving absorbent part may be of elongate shape.

For preference, the receiving absorbent part is formed of an absorbent layer covered by a wound-contact interface layer, which avoids impairing the wound healing process when the dressing is removed. This interface layer is preferably covered by a temporary protective film which is removed prior to use.

Dressings known by the name of "wound-contact layer interface dressings" such as, for example, the products marketed by the companies Laboratoires URGO and MOLNLYCKE HEALTH CARE under the trade names URGOTUL® and MEPITEL® respectively may be used for such a layer.

It is also possible to use polymer-based perforated layers of hydrophobic or hydrophilic formulation but which are non-absorbent or not very absorbent. These formulations may be adherent or nonadherent.

It is preferable to use microadherent or nonadherent formulations. Such formulations are well known to those skilled in the art and are made for example based on silicone gel(s), pressure-sensitive silicone adhesive(s) or compositions containing a block polymer elastomer of the poly (styrene-olefin-styrene) type, a plasticizer such as a mineral oil and a small quantity of hydrocolloid(s) in order to create a moist environment that encourages the healing process without making the composition absorbent in order to avoid blocking the holes. Such microadherent formulations are used for example in the dressings marketed by the company Laboratoires URGO under the trade names URGO-CLEAN® and URGOTUL ABSORB®.

According to possible alternative forms, these wound-contact layer interface dressings and these perforated layers of hydrophobic or hydrophilic formulation are combined with permeable materials, particularly non-absorbent nonwovens, which are incorporated between the absorbent layer and the additional layers.

As mentioned above, the fluidic-propagation paths leading from the collection zone to the retention and/or evaporation zone are defined by a transfer structure.

Transverse Structure

The transfer structure is also referred to as the "distribution layer".

Its role is not to retain the liquids but to allow them to spread.

The transfer structure is preferably less absorbent on the one hand than any receiving absorbent part there might be and on the other hand than any absorbent part forming a retention and/or evaporation zone that might be present. The transfer structure preferably has a maximum absorption value less than 500 or even 1000 $g/m^2$.

For preference, its thickness is comprised between 50 and 1000 μm, better still between 300 and 500 μm.

The longest dimension of the transfer structure is, for example, greater than or equal to 10 cm, or even 30 cm, the longest dimension then being the length.

For preference, the transfer structure contains or is made up of a fibrous material based on absorbent fibers, so as to allow effective drainage of the liquid. In this type of material, the liquid propagating gradually along the fibers is what produces a drainage effect.

By way of example of such materials, mention may be made of materials based on absorbent fibers of plant origin, such as viscose, cellulose or derivatives thereof. These materials may take the form of knits, wovens or nonwovens, obtained by a dry airlaid route or by a wet route, like papers.

In the context of the present invention, nonwovens and papers are preferred. Among the nonwovens, preference is given to those based on absorbent fibers such as viscose or cellulose associated with non-absorbent fibers such as, for example, polyester or polyolefin fibers. By way of example of such nonwovens, mention may be made of the products marketed respectively by the companies Suominen Corp and Orsa under the trade names Fibrella® 2000 and Jettex® 1205 c, or Berkshire under the trade name DR870.

The transfer structure may take the form of at least three disjointed elements, directly in contact with a layer of an absorbent material of the receiving absorbent part, with no intermediate layer between them. As an alternative, an intermediate layer may be interposed, for example a perforated layer of a hydrophobic material, so as to reduce the risk of liquid returning to the receiving absorbent part. As an alternative, the collection zone may be defined by a portion of the transfer structure directly in contact with the wound or with the interposition of a wound-contact layer interface dressing.

The transfer structure may have elements defining fluidic-propagation paths which are closer together in the collection zone. These elements may lie in the same plane or conform to the relief of the region of the body or to the shape of the wound from which the physiological liquid to be collected originates.

When the transfer structure has disjointed elements which define respective fluidic-propagation paths, these elements may be cut from the same hydrophilic material, preferably containing absorbent fibers. These elements may be kept in a given geometric configuration by one or more adjacent layers of the article or by any other suitable means. If appropriate, the elements are assembled with one another with the interposition of barrier layers that at least partially, or better still completely, block the diffusion of the liquid from one element to the other.

Another way of creating the transfer structure is to apply a differentiated treatment to one and the same starting material, in sheet form. For example, a hydrophilic absorbent material such as a paper is treated by applying a hydrophobic material, for example a silicone resin, applied with a structure, notably in the form of lines, preferably continuous lines, delimiting fluidic-propagation paths between them. Each line of hydrophobic material then constitutes a fluidic barrier blocking the passage of the fluid from one path to another.

Support

The article may comprise a support which may define at least part of the exterior surface of the article.

The support is preferably impermeable to water and external pathogenic microorganisms while at the same time being permeable to water vapor, so as both to avoid contact between the wound and external liquids and bacteria and to avoid maceration of the wound. The support is then termed "impermeable and breathable".

The support is preferably thin and flexible, so as best to conform to the shape of the body and accompany the movements thereof without the risk of becoming detached. The support is advantageously conformable. Its thickness may be comprised between 100 and 600 μm, preferably between 250 and 500 μm.

The support may be made of a single material or an assembly of several materials.

The support may thus contain or consist of a film that is continuous and impermeable to liquids and bacteria but permeable to water vapor. By way of example of films that may be used, mention may be made of films made of polyetherurethane, of polyetheramide or polyetherester. The thickness of the film is, for example, comprised between 5 and 200 microns, preferably between 10 and 75 microns, more preferably still, between 10 and 50 microns.

The film advantageously has a moisture vapor transmission rate (MVTR) greater than 3 000 $g/m^2/24$ hours, preferably greater than or equal to 7 000 $g/m^2/24$ hours, more preferably still greater than or equal to 10 000 $g/m^2/24$ hours. A technique for measuring the moisture vapor transmission rate in contact with liquid is described in standard NF-EN 13726-2 (Chapter 3.3).

Such films are commonly used in the creation of dressings and are for example made of polyurethane films, such as the films marketed by the company Exopack Advanced Coating under the trade name INSPIRE.

The film may be replaced by a foam/film complex. The film may also be complexed with another material which then acts as a supporting framework to make the support more rigid.

Such a supporting framework may make it possible to make the support more rigid so that it does not curl up on itself after any potential peel-off protective films have been removed.

The supporting framework may be made of any perforated material such as a perforated film, a thermoplastic mesh, a textile such as a woven, a knit or a nonwoven for example, preferably an elastic one so that the article holds better on the skin.

When a perforated film is used to make the supporting framework, the film is for example made of polyethylene or a polypropylene. When a woven textile is used it is, for example, made of polyethylene terephthalate or of a polyamide. The grammage of the supporting framework is preferably comprised between 10 and 500 $g/m^2$, for example between 20 and 300 $g/m^2$. Dressings with such supporting framework supports are described in application WO 2012/140377.

The film or complex acting as a support may be assembled with the other layers of the dressing using a discontinuous adhesive so as not to affect the water vapor permeability of the film or of the complex.

The support may be used to hold the elements of the transfer structure in the desired layout; the liquid that diffuses into the elements cannot diffuse into the support in contact with them, which is impermeable, in order to pass from one element into the adjacent element.

Another subject of the invention is the use of the article according to the invention to absorb a physiological liquid other than the exudate from a wound. Thus, in exemplary embodiments of the invention, this invention applies to the creation of disposable nappies and feminine sanitary products.

Figure 2:
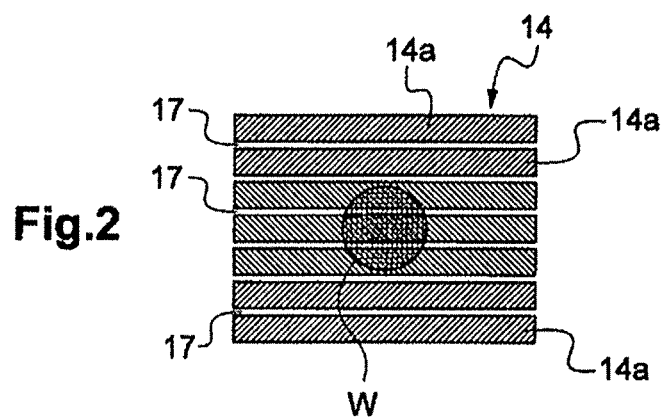
Figure 3:
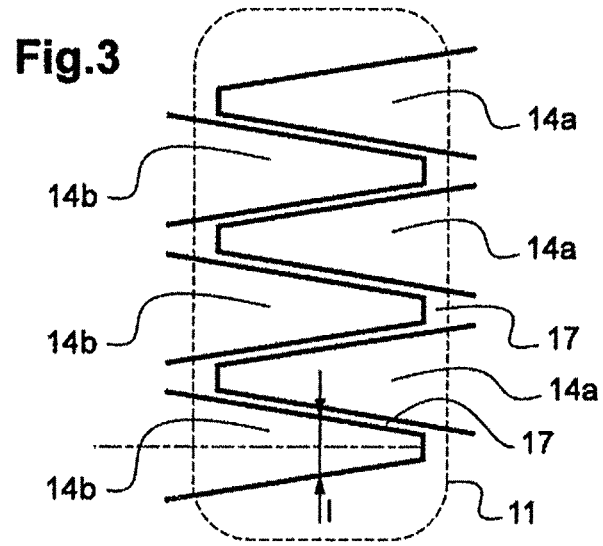

The invention may be better understood from reading the detailed description that follows, of some nonlimiting exemplary embodiments thereof and from studying the attached drawing in which:

FIG. 1 schematically and partially depicts, in cross section, one example of an article produced according to the invention, FIG. 2 depicts in isolation, in a view from above, the transfer structure of the example of FIG. 1, FIG. 3 illustrates an alternative form of embodiment of the transfer structure, FIGS. 4 to 6 are views similar to FIG. 2 of alternative forms of articles produced in accordance with the invention, FIG. 7 is a schematic and partial perspective view of another alternative form of embodiment of the article according to the invention, FIG. 8 is a schematic partial perspective view of another exemplary embodiment of the transfer structure, and FIGS. 9 and 10 are schematic and partial views from above of alternative forms of articles produced in accordance with the invention.

For the sake of clarity, the drawings are not always necessarily to scale. Likewise, certain elements may have been depicted with a slight spacing between them in the drawings whereas in real life they are in contact with one another.

The article 10 depicted in FIG. 1 is intended to be applied to part of a human or animal body, to absorb a physiological liquid such as an exudate. It is preferably a dressing intended to be applied to a wound W.

The article 10 may, as in the example illustrated, comprise a receiving absorbent part 11 intended to receive the exudate, defining an exudate collection zone 12, and at least one absorbent part forming a retention and/or evaporation zone, connected to the receiving absorbent part 11, by a transfer structure 14 according to the invention.

In order to reduce the risk of exudate returning toward the receiving absorbent part 11, the article 10 may comprise an intermediate layer as defined hereinabove, not depicted in the drawing, situated between the transfer structure 14 and the receiving absorbent part 11.

In the example illustrated, the article 10 comprises two absorbent parts 13a and 13b forming retention and/or evaporation zones, which are positioned respectively on either side of the receiving absorbent part 11.

The article 10 may also comprise a support 15 made of a layer impermeable to water and which may as illustrated cover the top of the parts 13a and 13b forming retention and/or evaporation zones and the transfer structure 14.

The receiving absorbent part 11, the transfer structure 14 and the support 15 are as defined in general earlier on.

The transfer structure 14 has draining properties that allow liquid to be transferred by diffusion from the receiving absorbent part 11 to the absorbent parts 13a and 13b forming retention and/or evaporation zones.

The transfer structure 14 may comprise several transfer elements 14a as illustrated in FIG. 2. These elements 14a in the example considered take the form of strips that are substantially parallel to one another and spaced apart by a gap 17.

Thus, the liquid may diffuse in each strip element 14a without diffusing from one element 14a to an adjacent element 14a, because of the presence of the gap 17 between the two. The gap 17 is an empty space, forming a fluidic barrier between two adjacent elements 14a.

The elements 14a make it possible to define a direction of drainage parallel to them and the liquid may thus be drained from the wound W toward the absorbent parts 13a and 13b between which the elements 14a extend.

In FIG. 2 it may be seen that just three elements 14a situated above the wound P are moistened with exudate, the other elements 14a remaining dry.

Avoiding lateral migration of the drained fluid thus avoids moistening the part of the transfer structure 14 which is not in contact with the bodily fluid.

In the case of a dressing, this then prevents the perilesional skin from coming into contact with the exudate. In the case of a female sanitary item or a disposable nappy, this reduces the risk of dry parts of the body close to the source of bodily fluid becoming wet.

The elements of the transfer structure 14 may contain absorbent fibers and offer, for transporting the exudate, a cross section that increases toward the part forming a retention and/or evaporation zone, as illustrated in FIG. 3.

More particularly, the elements of the transfer structure 14 may, when viewed from above, have a trapezoidal overall shape of which the width l increases linearly with increasing proximity to the absorbent part forming a retention and/or evaporation zone. This increase in the width l makes it possible to increase the rate at which the liquid diffuses, and therefore the quantity of liquid collected by the absorbent part forming a retention and/or evaporation zone, thereby making it possible to improve the performance of the article in the collection of exudate.

The fact that each element has an increasing width, measured perpendicular to its longitudinal axis, may also make it easier for elements to be imbricated and therefore provides the possibility of having transfer elements that are numerous and closely spaced, although disjointed, above the receiving absorbent part 11, as illustrated in FIG. 3. Moreover, it has been found that a transfer element with an increasing width allows optimized draining of a fluid.

It may be seen from this figure that the transfer structure 14 may be created with two sets of elements 14a and 14b which are imbricated with one another at the collection zone, the elements of one and the same set each defining a fluidic-propagation path.

A gap 17 between the elements 14a and 14b on the one hand and between the elements 14a or 14b on the other hand, makes it possible to avoid liquid migrating from an element 14 to an element 14b or between two 14a or 14b elements.

In an alternative form, the elements 14a are joined together at one end, which is superposed with the absorbent part forming a retention and/or evaporation zone 13a. The same is true of the elements 14b.

The transfer structure 14 may have a thickness that is substantially constant over its entire length. Alternatively, the thickness may vary.

The transfer elements 14a are, for example, of mutually parallel longitudinal axes Y, as are the elements 14b, as illustrated, but may also have different orientations.

The elements 14a, 14b, are, for example, cut in a single piece from a sheet of paper or nonwoven containing absorbent fibers as detailed above.

The absorbent parts forming retention and/or evaporation zones 13a and 13b may be disjointed, as illustrated in FIG. 2. As an alternative, they meet, and for example completely surround the receiving absorbent part 11.

The receiving absorbent part 11 and the transfer structure 14 may be assembled using an adhesive which is, for example, applied discontinuously. The same is true of the way in which the transfer structure 14 and the or each absorbent part forming a retention and/or evaporation zone are assembled.

The layout of the elements 14a, 14b may also be employed within an article that has no receiving absorbent part or no absorbent part forming a retention and/or evaporation zone. In that case, the liquid collection zone or the absorbent zone is defined directly by the transfer structure 14.

The transfer structure 14 may be used to evaporate the liquid with which it becomes laden, and the device may be created without an absorbent part forming a retention and/or evaporation zone in fluidic communication with the transfer structure.

FIG. 4 depicts an alternative form of embodiment in which the transfer structure 14 comprises radial transfer elements 14c extending from a central receiving absorbent part as far as a peripheral absorbent part 13 forming a retention and/or evaporation zone, which is annularly continuous, around the collection zone 11.

The elements 14c are, for example, arranged with even angular distribution about the receiving absorbent part 11 defining the collection zone.

The part 13 forming a retention and/or evaporation zone may be of angularly continuous annular shape, as illustrated in FIG. 4, or may be angularly discontinuous, as illustrated in FIG. 5, each element 14c of the transfer structure 14 then being able to communicate with a single respective reservoir-forming element 13c.

In this embodiment, each element 14c is isolated from the others by an empty space 17, the latter forming a fluidic barrier between two adjacent elements 14c.

In the alternative form illustrated in FIG. 6, the elements 14c of the transfer structure 14 are produced as a single piece with a central part 14d which becomes superposed on any absorbent part there might be defining the collection zone and with a peripheral part 14e which is connected to any absorbent part there may be forming a retention and/or evaporation zone and/or which defines an evaporation zone.

In the examples of FIGS. 4 to 6, the fluidic-propagation paths are defined by the radial transfer elements 14c, these for example being produced by cutting out from a sheet of a draining hydrophilic material. The liquid diffused in one of the elements 14c is unable to reach the adjacent elements, at least in the part situated between the collection zone and the retention and/or evaporation zone, because of the empty space 17.

In the examples of FIGS. 1 to 6 that have just been described, comprising a transfer structure 14 comprising several elements connecting the collection zone to one or more parts forming retention and/or evaporation zones, these elements are disjointed and not superposed.

As illustrated in FIG. 7, the elements of the transfer structure 14 may be defined by a single layer of a draining material, comprising hydrophobic parts 18 that make it possible to limit, or better still prevent, the circulation of liquid between hydrophilic parts 14f extending between the hydrophobic parts 18.

The hydrophilic parts 14f may, as illustrated, extend in the form of parallel strips, partially superposed at one end with a receiving absorbent part 11 defining the collection zone and at the other end with an absorbent part forming a retention and/or evaporation zone 13.

FIG. 8 illustrates the possibility of the transfer structure 14 comprising two elements 14g that are at least partially superposed. Each element 14g is covered on the top with a barrier layer 19 that is impermeable to water, so that liquid diffusing in the element 14g cannot reach the transfer element 14g that covers it.

A superposition of the elements 14g may make it possible to increase the throughput of the liquid diffused in the transfer structure, for the same skin area occupied.

As illustrated in FIGS. 9 and 10, the article may be produced in a single piece from a sheet of one and the same draining material.

The article comprises a central collection zone 14d and a peripheral retention and/or evaporation zone 14e, these being connected to one another by transfer zones 14c. The various zones are created by localized treatment 20 of the sheet of initial material, for example a hydrophobic treatment applied to a hydrophilic initial material in order to define zones, hatched in the figure, in which the fluid cannot propagate as illustrated in FIG. 9. In another example, the zones are defined following a hydrophilic treatment applied to a hydrophobic initial material in order to define the zones, hatched in the figure, in which the fluid may diffuse, as illustrated in FIG. 10.

The invention is not restricted to the examples illustrated.

In particular, the transfer structure may be embodied in still other forms.

The expression "comprising a" is to be understood as being synonymous with "comprising at least a".

The invention claimed is:

1. An article having bodily-fluid absorption properties, comprising at least three fluidic-propagation paths leading from a zone in which said fluid is collected to at least one retention and/or evaporation zone, each fluidic-propagation path being delimited by a fluidic barrier, the fluidic barrier opposing the passage of liquid from one fluidic-propagation path to another and extending between two adjacent fluidic-propagation paths, the fluidic-propagation paths being defined by a material containing absorbent fibers, and the retention and/or evaporation zone being defined by a material having a liquid absorption capacity greater than that of the fluidic-propagation paths.

2. The article as claimed in claim 1, the fluidic barrier comprising an empty space or a hydrophobic material.

3. The article as claimed in claim 1, said fluidic-propagation paths being defined by distinct elements of a transfer structure.

4. The article as claimed in claim 1, the fluidic-propagation paths being defined by elements arranged with an angular offset about a center of the article.

5. The article as claimed in claim 4, the fluidic-propagation paths being evenly angularly distributed.

6. The article as claimed in claim 1, the fluidic-propagation paths being defined by elements that are separated by a layer of a material impermeable to water.

7. The article claimed in claim 1, the fluidic-propagation paths being substantially parallel to one another.

8. The article as claimed in claim 7, comprising two sets of fluidic-propagation paths leading between a common fluid collection zone and two respective retention or evaporation zones, each retention or evaporation zone being specific to one of the two sets.

9. The article as claimed in claim 1, the retention or evaporation zone completely surrounding the collection zone.

10. The article as claimed in claim 9, the retention or evaporation zone being concentric with the collection zone.

11. The article as claimed in claim 1, the fluidic-propagation paths each opening at two opposite ends onto respective absorbent parts forming retention or evaporation zones.

12. The article as claimed in claim 1, the fluidic-propagation paths being defined by elements that are at least partially superposed.

13. The article as claimed in claim 1, constituting a dressing.

* * * * *